United States Patent [19]
Bacehowski et al.

[11] Patent Number: 4,910,147
[45] Date of Patent: Mar. 20, 1990

[54] CELL CULTURE MEDIA FLEXIBLE CONTAINER

[75] Inventors: David V. Bacehowski, Wildwood; Arnold C. Bilstad, Deerfield; David Fisher, Antioch; Robert Gliniecki, Richmond; Michael R. Keilman, Diamond Lake; Sidney T. Smith, Lake Forest, all of Ill.

[73] Assignee: Baxter International Inc., Deerfield, Ill.

[21] Appl. No.: 247,463

[22] Filed: Sep. 21, 1988

[51] Int. Cl.$^4$ .............................................. C12M 3/00
[52] U.S. Cl. ..................... 435/296; 435/284; 435/287; 435/286; 206/219; 206/484; 604/408; 215/247; 141/10
[58] Field of Search ............... 435/287, 296, 284, 286; 215/247, 365, DIG. 3; 604/403, 408, 409; 206/484, 484.1, 484.2; 141/10

[56] References Cited

U.S. PATENT DOCUMENTS

| | | |
|---|---|---|
| 3,191,474 | 6/1965 | Grevich et al. . |
| 3,276,447 | 10/1966 | Hamilton ............................ 604/403 |
| 3,306,327 | 2/1967 | Ilg . |
| 3,471,990 | 10/1969 | Bonuchi et al. . |
| 3,516,223 | 6/1970 | Andersen et al. . |
| 3,726,276 | 4/1973 | Schumann et al. . |
| 4,201,208 | 5/1980 | Cambio, Jr. . |
| 4,212,299 | 7/1980 | Yokokoji et al. . |
| 4,235,233 | 11/1980 | Mouwen . |
| 4,273,894 | 6/1981 | Mucke et al. . |
| 4,360,996 | 11/1982 | Rutter . |
| 4,381,776 | 5/1983 | Latham, Jr. . |
| 4,460,365 | 7/1984 | Ganshirt et al. . |
| 4,465,487 | 8/1984 | Nakamura et al. . |
| 4,479,989 | 10/1984 | Mahal . |
| 4,482,585 | 11/1984 | Ohodaira et al. . |
| 4,496,361 | 1/1985 | Kilkson . |
| 4,507,123 | 3/1985 | Yoshida . |
| 4,516,977 | 5/1985 | Hebert ............................ 604/403 X |
| 4,521,467 | 6/1985 | Berger ............................ 206/484 X |
| 4,528,220 | 7/1985 | Hwo . |
| 4,534,154 | 3/1985 | Gaubert . |
| 4,548,605 | 10/1985 | Iwamoto et al. . |
| 4,561,110 | 12/1985 | Herbert . |
| 4,602,910 | 7/1986 | Larkin . |
| 4,645,482 | 2/1987 | Yoshida ............................ 604/408 X |
| 4,657,540 | 4/1987 | Iwamoto et al. ..................... 604/408 |
| 4,657,542 | 4/1987 | Ohachi . |
| 4,661,100 | 8/1987 | Rechsteiner ..................... 604/317 X |
| 4,670,013 | 6/1987 | Barnes et al. ........................ 604/403 |
| 4,686,125 | 8/1987 | Johnston et al. . |
| 4,710,532 | 12/1987 | Hull et al. . |
| 4,723,956 | 2/1988 | Schnell et al. ................... 604/408 X |
| 4,797,309 | 1/1989 | Kammerer et al. ............ 206/484 X |

Primary Examiner—Larry Jones
Attorney, Agent, or Firm—Paul C. Flattery; Robert M. Barrett; Bradford R. L. Price

[57] ABSTRACT

A cell culture media container is provided. The container comprises a body constructed from flexible film and defining a containment area for containing the cell culture media, the body including a front face and a back face, the front and back face being sealed to each other along at least three sides thereof. The container includes a fill port for filling the containment area with cell culture media, the port being sealed to a face of the body and being so constructed and arranged that it extends from the face normal thereto. The container is constructed from a high barrier, optically clear, radiation sterilizable film.

24 Claims, 2 Drawing Sheets

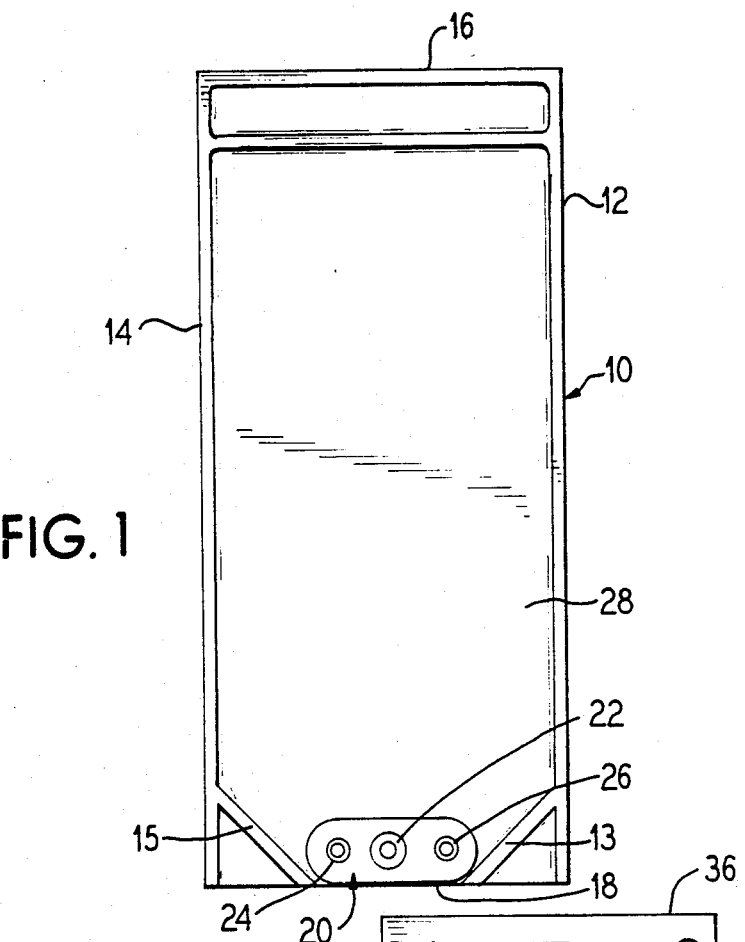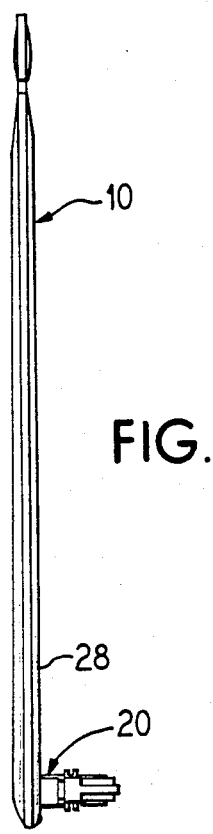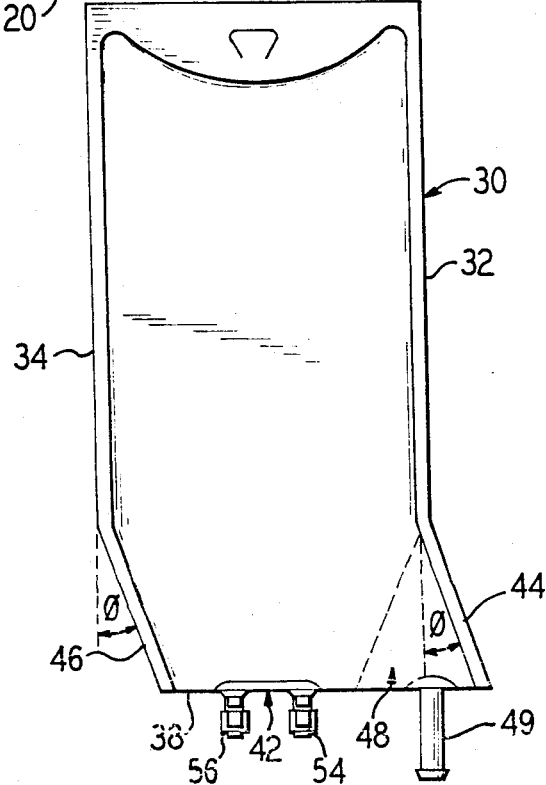

CELL CULTURE MEDIA FLEXIBLE CONTAINER

BACKGROUND OF THE INVENTION

The present invention relates, in general, to flexible containers. More specifically, the present invention relates to containers for containing cell culture media and other sensitive fluids.

Cell culture media is typically a solution of amino acids, electrolytes, and vitamins. Usually, the solution is supplemented with fetal bovine serum, which is believed to contain growth factors and other proteins that are essential to mammalian cell growth, without containing antibodies. Media is typically sold in either a liquid or powder form. If the media is sold in a powder form, it must be reconstituted prior to use.

Typically, liquid cell culture media is packaged in glass bottles, or containers, and stored at temperatures of approximately 2 to about 4° C. Glass bottles are used to package the cell culture media because of their barrier properties. Because amino acids are readily oxidized an oxygen barrier is needed. Furthermore, a carbon dioxide barrier is needed because typically a bicarbonate buffer system is used in the media. Moreover, it is critical that the interior surface of the container is inert because of the sensitivities of the cells to toxic leachables.

Cell culture media powder has been packaged in foil pouches or polyethylene bottles having screw caps. However, due to the structure of the pouches and/or bottles upon reconstitution the media must be placed in glass bottles. One of the disadvantages of powder media is that reconstituting the media and maintaining asepsis is labor intensive.

A typical "life cycle" for a glass bottle for containing cell culture media is as follows. The bottles are typically received from a glass manufacturer in bulk and inventoried by the media manufacturer. When needed, the bottles are unpacked, washed, and sterilized. The sterile bottles are then placed in a fill room where they are filled and capped. The filled bottles are conveyed from the fill room and inspected and labelled. The labelled bottles are placed in quarantine during testing of the product. Once a lot is released, the bottles are typically shipped to customers in specially designed corrugated cardboard containers. Customers must then unpack the bottles and store them in a refrigeration unit until use. When the bottles are used, they are uncapped using aseptic techniques and the media is removed by pouring it into another vessel or by pipetting. The glass bottle must then be disposed.

As illustrated above, the process of utilizing glass bottles for containing cell culture media has some clear disadvantages. Of course, the storage of glass bottles utilizes a large amount of warehouse space. This is not only a concern prior to the filling of the bottles with media but even after the bottles are filled The packaging density of glass bottles increases the warehouse space required in quarantine and release product.

Furthermore, the glass bottles are not presterilized and nonpyrogenic, therefore, prior to use, the bottles must be washed and sterilized. Moreover, due to the nature of glass, there is a possibility that the bottles will break or be damaged during shipping and handling.

Additionally, the typical techniques of removing the media from the glass bottles are time consuming and have a risk of contamination. Still a further disadvantage in using glass bottles is that there is a problem of disposing of the container after it has been emptied. An additional disadvantage of using a glass bottle is the cost associated with the handling of and the pre-filling processing of the containers.

Accordingly, there is a need for an improved container for containing cell culture media.

SUMMARY OF THE INVENTION

The present invention provides a cell culture media container comprising a body constructed from a flexible film that defines a containment area for containing the cell culture media. The body includes a front face and a back face. The front and back face are sealed to each other along at least three sides thereof. A fill port is provided for aseptically filling the containment area with cell culture media. The fill port is sealed to a face of the body and so constructed and arranged that it extends from the face, normal thereto.

The fill port can of course be filled in a nonaseptic manner in those applications where an aseptic condition is not required for the product to be housed in the container.

Preferably, the film is constructed from a high gas and water vapor barrier, optically clear, radiation sterilizable film. In an embodiment, the film is a laminate. In a further embodiment, the film is a polyolefin material. In a still further embodiment, the film is constructed from an inner layer of a polyethylene material, a core layer of a barrier material, and an outer layer of a polyolefin or polyester—based material.

Preferably, the port is constructed from a material that can be molded, has low gas permeability, and can be sonically welded. In an embodiment, the port is constructed from a polyolefin. In a preferred embodiment, the port is constructed from a polyethylene.

In a preferred embodiment, a container for housing a product constructed from a web of film and including an at least partially extending fill portion is provided. The container includes a top edge, a bottom edge, and side edges. The container is constructed so that portions of the side edges do not extend substantially normal to the top edge of the film. The fill segment is defined, in part, by a side edge portion of the container that extends from a remaining side edge portion of the container at an angle $\theta$ of greater than $0°$. The fill segment is designed to be, during the filling process of the container, sealed along a perimeter thereof from remaining portions of the container and severed therefrom. The fill port is secured to a portion of the fill segment.

A method for storing a product in a flexible container is also provided. The method comprises the steps of filling a fill port of a flexible container constructed from a web of film with a product, sealing a portion of the flexible container to define two sealed portions of the container, and severing the fill port and one of the sealed portions of the container from remaining portions of the container.

An advantage of the present invention is that it provides an improved cell culture media container.

A further advantage of the present invention is that it provides a cell culture media container having a port so constructed and arranged as to expedite the aseptic filling of the container with cell culture media.

A still further advantage of the present invention is that it provides a container that can be utilized with a semi-automatic aseptic fill machine.

Still, an advantage of the present invention is that it provides a fill port that is easily sealed to provide a sterile containment area.

Another advantage of the present invention is that the product is easily disposed of after a single use.

A further advantage of the present invention is that the design minimizes the potential for contamination by readily accommodating non-vented, aseptic solution transfer.

Another advantage of the present invention is that it provides a cell culture media container that can be stored in a minimal amount of space.

Another advantage of the present invention is that it provides a cell culture media container that, even when filled, requires a fraction of the space occupied by a typical glass container.

Additionally, an advantage of the present invention is that it provides a novel container construction.

A further advantage of the present invention is to provide an improved method for filling a container.

Additional features and advantages of the present invention will be apparent from the detailed description of the presently preferred embodiments and from the drawings.

BRIEF DESCRIPTION OF THE DRAWINGS

FIG. 1 illustrates a perspective view of an embodiment of a container for cell culture media of the present invention.

FIG. 2 illustrates a side elevational view of the container of FIG. 1.

FIG. 3 illustrates a perspective view of another embodiment of a container for cell culture media of the present invention.

DETAILED DESCRIPTION OF THE PRESENTLY PREFERRED EMBODIMENTS

Figure 4:
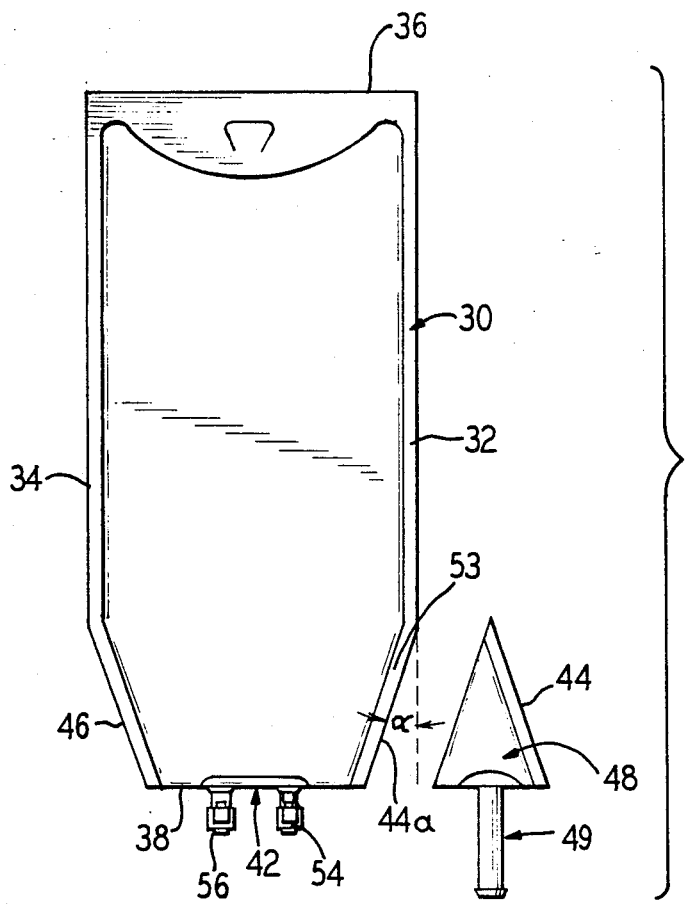
FIG. 4 illustrates a perspective view of the container of FIG. 3 after the fill portion of the container has been severed.
Figure 5A:
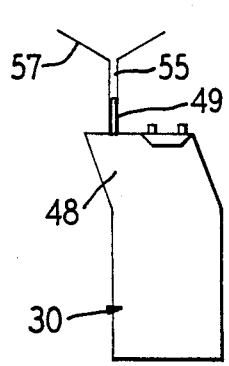
FIGS. 5a, 5b, 5c and 5d schematically illustrate the steps in a method of filling the container of FIG. 3.
Figure 5B:
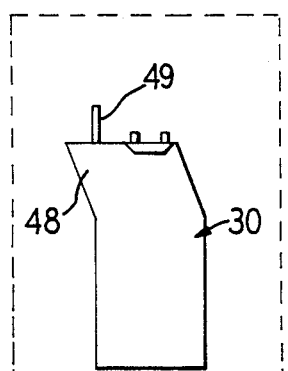
Figure 5C:
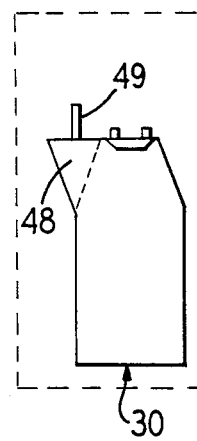
Figure 5D:
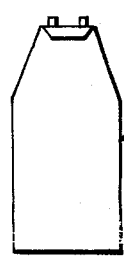

The present invention provides a flexible, high barrier container for cell culture media and other sensitive fluids. The container is constructed for aseptic fill applications. The container includes the following characteristics: radiation resistance; sterile, non-pyrogenic; shatterproof; nonvented; has an inert, nonreactive interior surface; high gas barrier properties; high moisture barrier properties; and high strength and flex-crack resistance properties.

Preferably, the container has an integrally attached high barrier fill port that is designed to interface with a semi-automatic, aseptic fill machine, especially the nozzle thereof. The container offers numerous advantages over typical glass cell culture media containers. To this end, the container in a nonfilled, collapsed condition, requires only a fraction of the space required by typical glass containers. Furthermore, the flexible container can be presterilized and is nonpyrogenic eliminating the need for washing and sterilization by the user. Moreover, the flexible containers, even when filled with product, have a higher packaging density than typical glass bottles thereby reducing the warehouse space required for the product in quarantine and release product. Also, the shatterproof nature of the flexible container substantially reduces breakage during shipping and handling.

Referring now to FIG. 1, a flexible container for housing cell culture media 10 is illustrated. The container includes sides 12 and 14, a top edge 16, and a bottom edge 18. The container 10 is constructed from a web of film that is folded along the edge 18 and sealed along edges 12, 14, and 16. Preferably, the web of film includes at least one thermal heat sealable layer allowing the edges of the web of film to be heat-sealed together.

In the embodiment of the container 10 illustrated, the container includes chevron seals 13 and 15. The chevron seals 13 and 15 improve the delivery characteristics of the container 10.

Preferably, the web of film from which the container is constructed has the following properties. It has very few to no leachables-extractables, and is therefore nonreactive with the solution to be housed therein. The film has high gas barrier properties and provides a good barrier to oxygen and carbon dioxide. The film possesses a low to nil water vapor transmission rate. The film has good clarity and therefore enables viewing of the contents. This is important in that it allows one to determine growth of contamination/pH indicator changes. Preferably, the film is able to withstand storage temperatures between ambient temperature to $-80°$ C. Moreover, the film is able to withstand ambient shipping temperatures and conditions. Still, the film will allow the media to be warmed prior to use. Usually cell culture media is warmed by immersing the container in a water bath that is heated to $37°$ C.

Preferably, the film is constructed from a material that includes a polyolefin material. Preferably, the film also includes a high barrier material. Polyvinylidene chloride and ethyl-vinyl alcohol (EVOH) have been found to function satisfactorily as a barrier material. Preferably, the film is a laminate including an outer layer, an inner layer, and a core layer. A polyolefin material preferably defines the inner layer, a barrier material defines the core layer, and a polyolefin or polyester-based material defines the outer layer. In a preferred embodiment, the outer and inner layers are polyethylene based materials, i.e., they include at least a polyethylene in the composition. Preferably, the layers are bonded together with a radiation resistant, bicompatibile adhesive.

By way of example, and not limitation, a film that has been found to function satisfactorily as a cell culture media container will now be set forth. The film is a laminate having: an outer layer constructed from approximately 5%, by weight, ethyl-vinyl acetate and approximately 95%, by weight, low density polyethylene; a core layer constructed from biaxially oriented ethyl-vinyl alcohol (EVOH); and an inner layer constructed from linear low density polyethylene. The film has the following, approximate, layer thicknesses: the outer layer is approximately 0.002 inches thick; the core layer is approximately 0.0005 inches thick; and the inner layer is approximately 0.002 inches thick. Such a film is sold by Curwood, Inc. of New London, Wisconsin as 6520 laminated film.

This film has been found to provide an inner layer that meets the criteria previously stated and has good thermal bonding properties. The core layer provides a layer having good barrier properties, especially with respect to gas transmission, and the outer layer provides the film with good strength and flex crack resistance. In the embodiment of the film given in this example, the layers are sealed together by a polyester adhesive. Of course, the above film is only presented by way of example and other components can be utilized for the film (as discussed previously), the film may include more or less than three layers, and the layers can have different thicknesses.

As illustrated in FIGS. 1 and 2, the container 10 includes a fitment 20. The fitment 20 provides means for accessing a containment area defined by the container for filling the container and/or accessing the contents of a filled container. To this end, in the embodiment illustrated in FIGS. 1 and 2, the fitment 20 includes a fill port 22 and access ports 24 and 26.

In constructing the container 10, in an embodiment, holes are punched in the film and the fill port 22 and access ports 24 and 26 are inserted therethrough and a top portion of the body of the fitment 20 is sealed to the film.

The fill port 22 is utilized to fill the container 10 with cell culture media. Preferably, the fill port 22 is constructed from a material that can be easily sealed. Accordingly, after the container 10 has been filled with cell culture media, the fill port 22 can be sealed enclosing the cell culture media within the container 10. In a preferred embodiment, the fill port 22 is constructed from a material that can be sonically welded. Preferably, the fill port 22 is constructed from a polyolefin. In an embodiment, the fill port 22 is constructed from a high density polyethylene.

Typically, in use, the container is filled by having a nozzle or other means inserted in the fill port and cell culture media fed therein. The nozzle or other means is then removed from the fill port and the fill port is sonically welded. This provides a container 10, containing cell culture media, that is sealed.

As illustrated, the fitment 20 includes access ports 24 and 26. It should be noted that although two access ports are illustrated on the fitment 20, more or less access ports can be utilized. Furthermore, if desired, the fill port 22 and access ports 24 and 26 can be secured to separate fitments.

The access ports 24 and 26 provide a means for accessing the contents of the container 10. To this end, the access ports 24 and 26 are designed to receive a standard spike/luer. Preferably, the access ports 24 and 26 are sealed by a removable cap and include a pierceable membrane that is pierced by a spike, or like means, when the container is accessed. Of course, other means of accessing the container via the access ports 24 and 26 can be utilized.

As illustrated in FIGS. 1 and 2, in contrast to a standard fitment and port arrangement, the container 10 of the present invention is constructed so that the fitment 20, and specifically the ports 22, 24, and 26 extend outwardly from a face 28 of the container 10. In typical flexible containers, the fitment or ports extend from the bottom edge of the container in a plane that is substantially parallel to a plane defined by the face of the container. By extending the ports 22, 24, and 26 of the fitment 20 outwardly from the face 28 of the container 10, i.e., normal to a plane defined by the face 28 of the container 10, an improved container is provided in that it affords a container that can be easily and cost effectively fabricated and filled with cell culture media utilizing a semi-automatic, aseptic fill machine. Further, the fitment arrangement 20 provides a container 10 from which the cell culture media stored therein can be easily accessed.

Referring to FIG. 3, another embodiment of the container 30 of the present invention is illustrated. Again, the container 30 is constructed from a flexible web of film having the same characteristics as set forth above for the embodiment of the container 10 illustrated in FIGS. 1 and 2. Likewise, the container 30 can be constructed from the films discussed above with respect to the previous embodiment of the container 10.

Similar to the previous embodiment of the container, the web of film is folded along an edge 38 and sealed on sides 32 and 34 and a top edge 36. However, in contrast to the previous embodiment illustrated in FIGS. 1 and 2, the side edges 32 and 34 do not extend for a length of the container 30 perpendicularly or normal to the top edge 36 of the container 30. Instead, portions of the side edges 44 and 46 extend outwardly, and inwardly, from remaining sides edges 32 and 34, respectively, and therefore, do not extend perpendicularly from the top edge 36.

As illustrated, the side edge 44 extends outwardly from remaining portions of the side edge 32 at an angle $\theta$ that is greater than $0°$. Preferably, the angle $\theta$ is greater than $0°$ but less than $90°$. The side edge portion 44 defines, with portions of the container 30, an at least partially extending fill segment 48. As discussed in more detail hereinafter, the fill segment 48 is utilized to fill the container with cell culture media and designed to be severed from the container 30 after the filling process. To this end, a fill port 49 is secured to the container 30 at a location in juxtaposition to the side edge portion 44 of the container 30.

As previously stated, a second side 34 of the container 30 includes a portion 46 that also does not extend along the container 30 perpendicularly to the top edge 36. In this regard, side edge portion 46 extends inwardly from the remaining side edge portions 34 at an angle $\phi$. Angle $\phi$ is greater than $0°$ but less than $90°$.

Referring to FIG. 4, the container 30, after it has been filled through the fill port 49, is illustrated. As illustrated, the container 30 has been sealed along a perimeter 53 segregating the fill segment 48 from remaining portions of the container, and the fill segment has been severed from the container 30. In an embodiment, the fill segment 48 is severed from the container 30 by means that severs the fill segment while sealing the container. As illustrated, once so severed, the container 30 includes a side edge portion 44a that now extends from the remaining side portions 32 inwardly at an angle $\alpha$ that is greater than $0°$ but less than $90°$. The container 30 illustrated in FIG. 4 has been filled and accordingly now is in a condition where it can be accessed by the user through access ports 54 and 56 of the fitment 42.

Referring now to FIG. 5, a schematic illustrating a method of filling the container 30 of FIG. 3 is illustrated. As illustrated, in step 5a, the container 30 is filled through a fill port 49 by a nozzle 55 of an aseptic fill machine 57. In step 5b, the fill port 49 is then sealed by sonic welding or some other means. In step 5c, the container 30 is sealed along a perimeter of the fill segment 48 by thermal sealing means. After the container 30 is so sealed, the fill segment 48 is then cut by a die or some other means. It should be noted, however, that means for contemporaneously sealing and severing the fill segment 48 can be utilized. 5d illustrates the filled container 30 that can now be accessed when desired.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A cell culture media container comprising:
   a body constructed from flexible film that comprises an inner layer constructed from a polyethylene material, a core layer constructed from a barrier material, and an outer layer constructed from a material chosen from the group consisting of polyethylene and polyester-based material, the body defining a containment area for containing the cell culture media and including a front face and a back face, the front and back face being sealed to each other along at least three sides thereof; and
   a fill port for receiving a nozzle means that fills the containment area with cell culture media, the port being sealed to a face of the body and being so constructed and arranged that it extends from the face normal thereto.

2. The cell culture media container of claim 1 wherein the film is a high barrier, optically clear, radiation sterilizable film.

3. The cell culture media container of claim 2 wherein the film is a laminate.

4. The cell culture media container of claim 1 wherein the fill port is constructed from a material that can be sonically welded.

5. The cell culture media container of claim 1 wherein the flexible film is constructed, at least in part, from a polyolefin.

6. The cell culture media container of claim 1 wherein the port is constructed from a moldable polyethylene.

7. A cell culture media container comprising:
   a body, constructed from a web of film folded onto itself and sealed on at least three sides to define a containment area to be filled with a cell culture media, the web of film comprising an inner layer constructed from a polyethylene material, a core layer constructed from a barrier layer, and an outer layer constructed from a material chosen from the group consisting of polyethylene and polyester-based material, the body including, prior to being filled with the cell culture media, two faces that lie in substantially parallel planes; and
   at least one port providing means for filling the containment area with cell culture media, the port being secured to a face of the body and extending outwardly therefrom normal to at least one plane defined by the faces of the body.

8. The cell culture media container of claim 7 wherein the fitment is constructed from a high density polyethylene.

9. The cell culture media container of claim 7 wherein the fitment is secured to the face of the body by having portions thereof being received within a hole punched in the web of film, and portions thereof extending outwardly from the hole.

10. The cell culture media container of claim 7 wherein the body includes at least one chevron seal for sealing a portion of the first face to a portion of the second face.

11. The cell culture media container of claim 7 wherein the barrier layer is constructed from a material chosen from the group consisting of polyvinylidene chloride and ethyl-vinyl alcohol.

12. The cell culture media container of claim 7 wherein the film includes an outer layer constructed from 5%, by weight, ethyl-vinyl acetate and 95%, by weight, polyethylene, a core layer constructed from ethyl-vinyl alcohol, and an inner layer constructed from polyethylene.

13. The cell culture media container of claim 12 wherein the film is a laminate and the layers are secured together by a polyester adhesive.

14. The cell culture media container of claim 7 including a second access port for accessing the contents of the containment area.

15. A container for housing product, the container constructed from a web of flexible film and comprising:
    a top edge, a bottom edge, and side edges, each of the side edges having a greater length than a length of either of the top edge or bottom edge and the side edges including portions thereof that do not extend perpendicular to the top edge, one portion of one of the side edges extending outwardly from a remaining portion of the edge at an angle $\theta$ that is greater than 0°, the container including a fill port.

16. The container of claim 15 wherein the portion of the side edge that extends outwardly defines, with portions of the body, a fill segment of the container, the fill port being secured to the fill segment of the container.

17. The container of claim 16 including an access port secured to the container at a location other than the fill amount of the container.

18. The container of claim 15 wherein one portion of one of the side edges extends inwardly from remaining portions of the side edge at an angle $\phi$ that is greater than 0° and less than 90°.

19. A method for storing a fluid in a flexible container comprising the steps of:
    at least partially filling a flexible container constructed from a web of film with a fluid, by feeding fluid into the container through a fill port in the container;
    sealing a portion of the flexible container to define two sealed portions, one of the portions including the fill port; and
    severing the sealed portion of the container having the fill port from remaining portions of the container.

20. The method of claim 19 including the step of sealing the fill port before sealing the portion of the container.

21. The product of the process of claim 20.

22. The method of claim 19 including the step of contemporaneously sealing and severing a portion of the bag.

23. The product of the process of claim 19.

24. A container for housing product made in accordance with the method of claim 19, the container constructed from a web of flexible film and further including a top-edge, a bottom edge, side edges, and a fill port.

* * * * *